United States Patent [19]

Haeckel et al.

[11] 4,206,231
[45] Jun. 3, 1980

[54] HYPOGLYCAEMICALLY ACTIVE 2-ALKYL- OR -ALKENYL-HYDRAZONO PROPIONIC ACID DERIVATIVES

[75] Inventors: Rainer Haeckel; Michael Oellerich, both of Hanover; Ruth Heerdt, Mannheim-Feudenheim; Manfred Hubner, Ludwigshafen am Rhein; Felix H. Schmidt, Mannheim-Seckenheim, all of Fed. Rep. of Germany

[73] Assignee: Boehringer Mannheim GmbH, Mannheim, Fed. Rep. of Germany

[21] Appl. No.: 934,291

[22] Filed: Aug. 17, 1978

[30] Foreign Application Priority Data

Sep. 1, 1977 [DE] Fed. Rep. of Germany ....... 2739380

[51] Int. Cl.² .................. A61K 31/195; C07C 101/02
[52] U.S. Cl. ..................................... 424/305; 424/319; 424/320; 424/314; 560/121; 560/125; 560/155; 560/168; 562/553; 562/560; 260/557 H; 260/561 A; 560/623; 560/124; 562/503; 562/505; 562/506; 562/507
[58] Field of Search ............... 562/553, 560, 503, 505, 562/506, 507; 560/155, 168, 169, 121, 123, 125, 124; 424/319, 305, 320; 260/557 H, 561 A

[56] References Cited

U.S. PATENT DOCUMENTS 4,136,196   1/1979   Haeckel et al. .................. 424/319

OTHER PUBLICATIONS

N. Kizhner et al., "Action of Hydrazine Hydrate on Cyclohexanone, " J. Russ. Phys. Chem. Soc. 43, pp. 577-82. (See Chemical Abstracts vol. 6 (1912), p. 347.
Andrews, S. D. et al., "Cycloadditions Part III" J. Chem. Soc. (C) (1969) at p. 2448.

*Primary Examiner*—Bernard Helfin
*Attorney, Agent, or Firm*—Sprung, Felfe, Horn, Lynch & Kramer

[57] ABSTRACT

A 2-hydrazonopropionic acid derivative of the formula

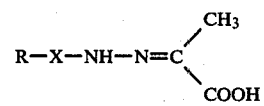

wherein
  R is an aliphatic hydrocarbon radical, and
  X is a valency bond or a divalent aliphatic hydrocarbon radical containing up to 4 carbon atoms, with the proviso that when X is a valency bond, R cannot be saturated cycloalkyl, or a physiologically compatible salt, lower alkyl ester or amide thereof, which exhibit hypoglycaemic activity.

11 Claims, No Drawings

HYPOGLYCAEMICALLY ACTIVE 2-ALKYL- OR -ALKENYL-HYDRAZONO PROPIONIC ACID DERIVATIVES

The present invention is concerned with 2-hydroazonopropionic acid derivatives and with the preparation thereof.

It is known that some monoamide oxidase inhibitors, for example phenelzine (2-phenylethyl hydrazine) and mebanazine (1-phenyl-ethyl-hydrazine), can, in high dosages, be hypoglycaemically active (see P.I. Adnitt, Hypoglycemic action of monoamino oxidase inhibitors, Diabetes, 17, 628–633/1968; L. Wickstrom and K. Petterson, Treatment of diabetics with monoamino oxidase inhibitors, Lancet, 2, 995–997/1964; and A. J. Cooper and K. M. G. Reddie, Hypotensive collapse and hypoglycaemia after mebanazine-a monoamine oxidase inhibitor, Lancet, 1, 1133–1135/1964).

However, the main action is the inhibiting action of the monoamine oxidases (MAO) so that these compounds have certainly been used for the therapy of psychic illnesses (see H. M. van Praag and B. Leijnse. The influence of some antidepressives of the hydrazine type on the glucose metabolism of depressed patients, Clin. Chim. Acta, 8, 466–475/1963) but it has not been possible to use them as blood sugar lowering medicaments.

Thus, the problem exists of finding compounds which exhibit a hypoglycaemic action in the dosage range in which MAO inhibition does not occur at all or only to an insignificant extent.

Surprisingly, we have now found that the hydrazones of pyruvic acid with a hydrazine component which differs from that of phenelzine exhibit, in comparison with the corresponding hydrazines, a considerably increased hypoglycaemic action, whereas the MAO inhibiting action is almost completely suppressed.

Thus, according to the present invention, there are provided new propionic acid derivatives of the general formula:

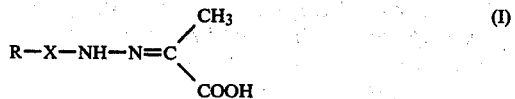

wherein R is a straight-chained, branched or cyclic saturated or unsaturated aliphatic hydrocarbon radical and X is a valency bond or a straight-chained or branched, saturated or unsaturated divalent aliphatic hydrocarbon radical containing up to 4 carbon atoms, with the proviso that when X is a valency bond, R cannot be a saturated cycloalkyl radical; and the physiologically acceptable salts, esters and amides thereof.

The compound 2-(cyclohexyl-hydrazono)-propionic acid excluded from the scope of the present invention is known from the literature (see Chem. Zentralblatt, 1911, II, 362).

However, pharmacological investigations have shown that this compound is ineffective in comparison with the compounds according to the present invention.

The straight-chained or branched, saturated or unsaturated aliphatic hydrocarbon radicals of the substituent R can contain up to 18 carbon atoms, preferred straight-chained saturated alkyl radicals including the methyl, ethyl, n-propyl, n-butyl, n-pentyl, n-hexyl, n-heptyl, n-octyl, n-nonyl, n-decyl, n-undecyl, n-dodecyl, n-tridecyl and n-tetradecyl radicals. Preferred branched saturated alkyl radicals include the isopropyl, isobutyl, sec.-butyl, tert.-butyl, isopentyl, isohexyl, 2-ethylbutyl, 3,3-dimethylbutyl, 1-methylhexyl, 4-methylhexyl, 5-methylhexyl, 2-ethylhexyl, 3,5-dimethylhexyl and 3-methyloctyl radicals.

Straight-chained or branched unsaturated aliphatic hydrocarbon radicals are preferably the allyl, 3-butenyl, 3-pentenyl, 2-, 3-, 4- or 5-hexenyl, 9-decenyl, 2-methylallyl, 3,7-dimethyl-6-octenyl, 2-propynyl, 2-butynyl and 2-hexynyl radicals.

Saturated and unsaturated cyclic aliphatic hydrocarbon radicals of the substituent R are carbocyclenes with 3 to 8 carbon atoms, the preferred saturated carbocyclic radicals including the cyclopentyl, cyclohexyl and cycloheptyl radicals and the preferred unsaturated carbocyclic radicals including the 1-, 2- and 3-cyclohexen-2-yl radicals.

The present invention includes within its scope all stereoisomeric forms of the compounds of general formula (I) which can exist on the basis of asymmetric carbon atoms and/or double bonds (C=C and C=N) which are present in some of the compounds.

The new compounds of general formula (I) according to the present invention can be prepared, for example, by reacting a hydrazine of the general formula:

in which R and X have the same meanings as above, or a salt thereof with a propionic acid derivative of the general formula:

in which Y and Y' are halogen atoms or alkoxy radicals or together represent an oxygen atom and R' is a hydroxyl group, a lower alkoxy radical or an optionally substituted amino group, or with a salt of such a propionic acid derivative, whereafter, if desired, when an acid is obtained it is converted into a salt, ester or amide or when an acid derivative is obtained, the free acid is liberated therefrom.

When the substituents Y and Y' in compounds of general formula (III) are halogen atoms, then they are fluorine, chlorine, bromine or iodine atoms, chlorine and bromine atoms being preferred. When the substituents Y, Y' and R' are alkoxy radicals, then they can contain up to 4 carbon atoms, the methoxy and ethoxy radicals being preferred.

In carrying out this process, the substituted hydrazine (II) or an appropriate salt thereof is reacted in an appropriate polar solvent, for example water, a lower alcohol or acetic acid, with a propionic acid derivative (III) or preferably with a salt thereof and the reaction mixture adjusted to a weakly acid pH, possibly with the help of a buffer, such as sodium acetate. The reaction can be carried out at ambient temperature but can also be carried out with heating. The hydrazones (I) can be filtered off from the reaction mixture in the form of sparingly soluble compounds or they can be extracted with appropriate solvents, for example non-polar solvents.

It is also possible to prepare the substituted hydrazine (II) in a one-pot process, for example from an amine by reaction with hydroxylamine-O-sulphonic acid, and, after the addition of the propionic acid derivative (III), the desired hydrazone is precipitated out.

Some of the substituted hydrazines and the salts thereof are new compounds. Generally, it is not necessary to prepare them in pure form so that the crude products obtained can be employed. The substituted hydrazines can be prepared in known manner, for example by the reaction of hydrazine with an appropriate alkyl halide.

The physiologically acceptable salts are preferably the alkali metal, alkaline earth metal and ammonium salts, as well as salts with blood sugar-sinking biguanides. These salts can be prepared in known manner, for example by reacting the acids with appropriate free bases, carbonates or alcoholates.

The esters obtained as intermediates in the case of the above-described process can be isolated or, if desired, saponified directly to give the corresponding carboxylic acids. On the other hand, the carboxylic acids obtained can again be reacted in known manner to give the desired esters. The saponification of the esters is preferably carried out in an alkaline medium. Generally speaking, as esters of the carboxylic acids of general formula (I) there are to be understood, within the scope of the present invention, the reaction products of the carboxylic acids with alcohols. However, the esters with low molecular weight monohydroxy alcohols, for example methanol, ethanol, propanol and isopropanol, are preferred.

The amides of general formula (I) according to the present invention can be prepared in known manner from the carboxylic acids or from reactive derivatives thereof by reaction with amines. The amine components can be, for example, ammonia and mono- and dialkylamines, especially lower alkyl amines, as well as amino acids, such as carboxy-substituted lower alkyl amines, arylamines, alkylarylamines and aralkylamines, specific examples thereof including p-aminobenzoic acid, anthranilic acid, phenylalanine, α- and and β-alanine, serine, valine, glycine, arginine and the like.

The blood sugar-lowering compositions according to the present invention include all conventional forms suitable for oral and parenteral administration, for example tablets, capsules, dragees, syrups, solutions, suspensions, drops, suppositories and the like. For this purpose, the active material is admixed with solid or liquid carrier materials and then subsequently brought into the desired form. Solid carrier materials include, for example, starch, lactose, methyl cellulose, talc, highly dispersed silicic acid, high molecular weight fatty acids (for example stearic acid), gelatine, agar-agar, calcium phosphate, magnesium stearate, animal and vegetable fats and solid high molecular weight polymers (for example polyethylene glycols). Compositions suitable for oral administration can, if desired, contain flavoring and/or sweetening agents.

As injection medium, it is preferable to use water which contains the additives usual in the case of injection solutions, such as stabilizing agents, solubilizing agents and/or buffers. Additives of this kind include, for example, acetate and tartrate buffers, ethanol, complex-forming agents (such as ethylenediamine-tetraacetic acid and the non-toxic salts thereof) and high molecular weight polymers (such as liquid polyethylene oxide) for viscosity regulation.

Preferred compounds according to the present invention are, apart from those mentioned in the examples, also the following compounds:
2-(2-butynylhydrazono)-propionic acid
2-(3,5-dimethylhexylhydrazono)-propionic acid
2-(3,7-dimethyl-6-octenylhydrazono)-propionic acid
2-[2-(1-cyclohexen-1-yl)-ethylhydrazono]-propionic acid
2-(3-cyclohexyl-2-methyl-2-propenylhydrazono)-propionic acid
2-[2-(2-cyclohexen-1-yl)-ethylhydrazono]-propionic acid
2-(2-propynylhydrazono)-propionic acid
2-(2-hexynylhydrazono)-propionic acid
2-(3-pentenylhydrazono)-propionic acid and
2-[3-(3-cyclohexen-1-yl)-2-methyl-2-propenylhydrazono]-propionic acid.

The following examples are given for the purpose of illustrating the present invention:

EXAMPLE 1

2-(2-Cyclohexyl-ethylhydrazono)-propionic acid 2.7 g. (2-Cyclohexylethyl)-hydrazine sulphate (m.p. 185°–187° C. (decomp.)) are dissolved in 50 ml. water and mixed, while stirring, at ambient temperature with a solution of 1.1 g. pyruvic acid and 3.0 g. sodium acetate trihydrate in 10 ml. water. An oil initially separates out which quickly crystallizes. The substance is filtered off with suction, dissolved in water, with the addition of 6 ml. 2 N aqueous sodium hydroxide solution, and then slowly acidified with 2 N hydrochloric acid. The first amount of precipitate obtained contains impurities: it is filtered off with suction and discarded. Upon further acidification, the main amount of pure product precipitates out, which is filtered off with suction and dried in a desiccator over anhydrous calcium chloride. There is obtained 1.6 g. 2-(2-cyclohexylethylhydrazono)-propionic acid; m.p. 47° C. The yield is 67% of theory.

In an analogous manner, there are obtained by the reaction of pyruvic acid:

(a) with isobutylhydrazine sulphate (m.p. 127° C. (decomp.))
2-(isobutylhydrazono)-propionic acid
m.p. 88° C. (recrystallized from isooctane);
(b) with methylallylhydrazine oxalate (m.p. 160°–161° C. (decomp.))
2-(methylallylhydrazono)-propionic acid;
m.p. 68°–69° C. (recrystallized from isooctane and toluene);
(c) with propylhydrazine oxalate
2-(propylhydrazono)-propionic acid;
m.p. 56°–58° C. (recrystallized from ligroin and toluene);
(d) with isopentylhydrazine hydrochloride (m.p. 128°–130° C. (decomp.))
2-(isopentylhydrazono)-propionic acid;
m.p. 48°–50° C. (recrystallized from isooctane);
(e) with octylhydrazine hydrochloride
2-(octylhydrazono)-propionic acid;
m.p. 37°–38° C.;
(f) with cyclohexylmethyl)-hydrazine hydrochloride
2-(cyclohexylmethyl-hydrazono)-propionic acid;
m.p. 81°–82° C. (recrystallized from isooctane and toluene);
(g) with isopropylhydrazine hydrochloride
2-(isopropylhydrazono)-propionic acid;
m.p. 83°–84° C. (recrystallized from ligroin);
(h) with allylhydrazine hydrochloride
2-(allylhydrazono)-propionic acid;
m.p. 47°–48° C. (recrystallized from methylene chloride);
(i) with butylhydrazine sulphate 2-(butylhydrazono)-propionic acid;
m.p. 56°–57° C. (recrystallized from cyclohexane);
(j) with sec.-butylhydrazine sulphate
2-(sec.-butylhydrazono)-propionic acid;
m.p. 67°–68° C. (dissolved in aqueous sodium carbonate solution and precipitated out again with hydrochloric acid);
(k) with tert.-butylhydrazine hydrochloride
2-(tert.-butylhydrazono)-propionic acid;
m.p. 99°–100° C. (recrystallized from isopropanol and water);
(l) with hexylhydrazine hydrochloride
2-(hexylhydrazono)-propionic acid
m.p. 44° C. (dissolved in aqueous sodium carbonate solution and precipitated out again with hydrochloric acid);
(m) with 4-methylpentylhydrazine hydrochloride (crude product)
2-(4-methylpentylhydrazono)-propionic acid; oil;
(n) with 2-ethyl-butylhydrazine hydrochloride (m.p. 118°–125° C. (crude product)
2-(2-ethylbutylhydrazono)-propionic acid;
m.p. 83°–86° C. (recrystallized from isopropanol and water);
(o) with 5-hexenylhydrazine hydrochloride (m.p. 130°–135° C.) (crude product)
2-(5-hexenylhydrazono)-propionic acid; oil;
(p) with heptylhydrazine hydrochloride
2-(heptylhydrazono)-propionic acid;
m.p. 48°–49° C. (recrystallized from ligroin);
(q) with cyclopentylhydrazine
2-(cyclopentylhydrazono)-propionic acid;
m.p. 87°–88° C. (recrystallized from isooctane and toluene);
(r) with (2-cyclopentylethyl)-hydrazine hydrochloride
(m.p. 160° C.) (crude product)
2-(2-cyclopentylethylhydrazono)-propionic acid;
m.p. 64°–65° C. (recrystallized from diethyl ether and ligroin);
(s) with 2-(3-cyclohexen-1-yl)-ethylhydrazine hydrochloride
(m.p. 98°–138° C.) (crude product)
2-[2-(3-cyclohexen-1-yl)-ethylhydrazono]-propionic acid;
m.p. 67°–68° C. (recrystallized from isopropanol and water);
(t) with 2-cycloheptylethylhydrazine hydrochloride (m.p. 132°–145° C.) (crude product)
2-(2-cycloheptylethylhydrazono)-propionic acid;
m.p. 59°–61° C. (recrystallized from cyclohexane);
(u) with decylhydrazine hydrochloride (m.p. 94° C. (decomp.))
2-(decylhydrazono)-propionic acid;
m.p. 48°–49° C. (recrystallized from isooctane);
(v) with nonylhydrazine hydrochloride (m.p. 115° C.) (decomp.)
2-(nonylhydrazono)-propionic acid;
m.p. 46°–47° C. (recrystallized from isooctane); and
(w) with (3-cyclohexyl-propyl)-hydrazine hydrochloride
(m.p. 220°–225° C.)
2-(3-cyclohexylpropylhydrazono)-propionic acid; oil.

EXAMPLE 2

Sodium 2-(pentylhydrazono)-propionate 2.3 g. Pentylhydrazine hydrochloride are dissolved in 10 ml. water and mixed with a solution of 1.5 g. pyruvic acid and 2.2 g. sodium acetate in 5 ml. water, an oil being formed. The reaction mixture is stirred for about one hour, the oil is extracted with methylene chloride and the solution is washed with water, dried with anhydrous sodium sulphate and the methylene chloride evaporated. The oily residue is dissolved in 8 ml. ethanol and, while stirring, 3.0 ml. of a 30% sodium methylate solution in methanol added thereto. The sodium 2-(pentylhydrazono)-propionate formed separates out and is filtered off with suction and then washed first with a little ethanol and then with diethyl ether. There are obtained 1.9 g. (59% of theory) sodium 2-(pentylhydrazono)-propionate; m.p. 225°–228° C. (decomp.).

In an analogous manner, there are obtained by the reaction of pyruvic acid
(a) with (2-cyclohexylethyl)-hydrazine sulphate and subsequent preparation of the sodium salt
sodium 2-(2-cyclohexyl-ethylhydrazono)-propionate;
m.p. 230°–233° C. (decomp.); and
(b) with (3-cyclohexyl-propyl)-hydrazine hydrochloride
(m.p. 220°–225° C.) and subsequent preparation of the sodium salt
sodium 2-(3-cyclohexyl-propylhydrazono)-propionate;
m.p. 224°–226° C. (decomp.).

EXAMPLE 3

In a manner analogous to that described in Example 1, there are obtained by the reaction of pyruvic acid
(a) with 9-decenylhydrazine hydrochloride (crude product)
2-(9-decenylhydrazono)-propionic acid;
m.p. 39°–41° C. (recrystallized from hexane);
(b) with 2-hexenylhydrazine oxalate (m.p. 166°–167° C.)
2-(2-hexenylhydrazono)-propionic acid;
oil;
(c) with methylhydrazine sulphate
2-(methylhydrazono)-propionic acid;
m.p. 89°–91° C. (recrystallized from isopropanol and isooctane); and
(d) with 5-methylhexylhydrazine hydrochloride (m.p. 184°–188° C.) (crude product)
2-(5-methylhexylhydrazono)-propionic acid;
oil.

EXAMPLE 4

2-(Decylhydrazono)-propionamide 6.5 g. Decylhydrazine dihydrochloride are dissolved in 30 ml. water and mixed with a solution of 2.3 g. pyruvic acid amide in 40 ml. water. The pH is adjusted to about 3 by the addition of a dilute aqueous solution of sodium hydroxide and the solution left to stand for 16 hours in a refrigerator, the desired product thereby crystallizing out. It is filtered off with suction and recrystallized from isooctane. There are obtained 3.3 g. (51.6% of theory) 2-(decylhydrazono)-propionamide; m.p. 64° C. (decomp.).

EXAMPLE 5

Ethyl 2-(heptylhydrazono)-propionate 4.0 g. Heptylhydrazine hydrochloride are dissolved in 40 ml. ethanol and 2.3 g. ethyl pyruvate added thereto. The solution is left to stand for 20 minutes at ambient temperature, then mixed with 160 ml. water and the oil which separates out is extracted with diethyl ether. The ethereal solution is washed several times with a 2 N aqueous sodium carbonate solution and then with water, dried over anhydrous sodium sulphate and evaporated. The ethyl 2-(heptylhydrazono)-propionate obtained as residue does not crystallize. The yield is 3.7 g. (82.4% of theory).

In an analogous manner, there is obtained, with the use of nonylhydrazino hydrochloride and methyl pyruvate, methyl 2-(nonylhydrazono)-propionate in the form of an oil.

EXAMPLE 6

In a manner analogous to that described in Example 1, there are obtained by the reaction of pyruvic acid (a) with 4-hexenylhydrazine hydrochloride (free base b.p. 82°–89° C./14 mm.Hg; the hydrochloride is hygroscopic)
2-(4-hexenylhydrazono)-propionic acid;
oil;
the compound contains 0.6 mol water;

(b) with octadecylhydrazine dihydrochloride (m.p. 264° C. (decomp.) after sintering at 88° C.)
2-(octadecylhydrazono)-propionic acid;
m.p. 80° C. (recrystallized from isooctane);

(c) with 3-butenylhydrazine hydrochloride (crude product)
2-(3-butenylhydrazono)-propionic acid;
oil;

(d) with 3,3-dimethylbutylhydrazine hydrochloride (m.p. 213°–214° C.)
2-(3,3-dimethylbutylhydrazono)-propionic acid;
m.p. 95° C. (recrystallized from isooctane);

(e) with 3-methyloctylhydrazine oxalate (m.p. 190° C. (decomp.))
2-(3-methyl-octylhydrazono)-propionic acid;
oil;

(f) with 3-cyclohexyl-2-propenylhydrazine hydrochloride
(m.p. 165° C. (decomp.))
2-(3-cyclohexyl-2-propenylhydrazono)-propionic acid;
oil;

(g) with dodecylhydrazine dihydrochloride (m.p. 210° C. (decomp.) after sintering at 80° C.)
2-(dodecylhydrazono)-propionic acid;
m.p. 60°–61° C. (recrystallized from isooctane);

(h) with 4-methylhexylhydrazine dihydrochloride (hygroscopic; free base b.p. 86°–88° C./13 mm.Hg)
2-(4-methylhexylhydrazona)-propionic acid;
oil;

(i) with 1-methylhexylhydrazine oxalate (m.p. 95° C.)
2-(1-methylhexylhydrazono)-propionic acid;
oil;

(j) with (2-ethylhexyl)-hydrazine (free base b.p. 56°–60° C./0.1 mm.Hg)
2-(2-ethylhexylhydrazono)-propionic acid;
oil;

(k) with (3-hexenyl)-hydrazine hydrochloride (m.p. 166°–167° C.)
2-(3-hexenylhydrazono)-propionic acid;
oil; and (l) with (3-cyclopentyl-propyl)-hydrazine hydrochloride (m.p. 197°–202° C.)
2-(3-cyclopentyl-propylhydrazone)-propionic acid;
oil.

EXAMPLE 7

In a manner analogous to that described in Example 2, by the reaction of pyruvic acid with 3-cyclohexyl-2-methyl-2-propenylhydrazine hydrochloride (oil) and subsequent preparation of the sodium salt, there is obtained sodium 2-(3-cyclohexyl-2-methyl-2-propenylhydrazono)-propionate; m.p. 266°–268° C. (decomp.) (recrystallized from ethanol).

The novel compounds may be administered by themselves or in conjunction with carriers which are pharmacologically acceptable, either active or inert. The dosage units are about 0.2 to 2 grams per day for an adult or about 3–30 mg/kg per day although higher or lower dosages can be used. Rather than a single dose it is preferable if the compounds are administered in the course of a day, i.e., about four applications of 100 mg. each at spaced time intervals or 8 of about 50 mg. each. A convenient form of administration is in a gelatine capsule.

The dosage of the novel compounds of the present invention for the treatment of diabetes depends in the main on the age, weight, and condition of the patient being treated. The preferable form of administration is via the oral route in connection with which dosage units containing 50–500 mg. of active compound in combination with a suitable pharmaceutical diluent is employed. One or two unit dosages are good from one to four times a day.

For the preparation of pharmaceutical compositions, at least one of the new compounds (I) is mixed with a solid or liquid pharmaceutical carrier or diluent and optionally with an odoriferous, flavoring and/or coloring material and formed, for example, into tablets or dragees, or with the addition of appropriate adjuvants, suspended or dissolved in water or in an oil, for example, olive oil.

The compounds (I) can be administered orally or parenterally in liquid or solid form. As injection medium, it is preferred to use water which contains the stabilizing agents, solubilizing agents and/or buffers, conventional for injection solutions. Additives of this type include, for example, tartrate and borate buffers, ethanol, dimethyl sulphoxide, complex-forming agents (such as ethylene diamine-tetraacetic acid), high molecular weight polymers (such as liquid polyethylene oxide) for viscosity regulation or polyoxyethylene derivatives of sorbitan anhydrides.

Solid carrier materials include, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and sweetening agents.

As noted hereinabove the material administered may be the acid or a salt, ester or amide thereof. It is believed that due to hydrolysis in the body the active material is in all these instances the same, viz. probably the acid.

TEST PROTOCOL

In order to illustrate the pharmacological properties of the compounds according to the invention, the blood sugar lowering effect was determined and compared with some corresponding hydrazines. The new compounds lower the blood sugar at a lower concentration than the corresponding hydrazines, so that they are suitable as anti-diabetics.

Conduction of the blood sugar tests

Metabolically healthy, cross-bred, fasting guinea pigs were injected with the substances as aqueous solutions of their sodium salts, i.p. A control group receives equivalent amounts of an isotonic NaCl solution. Directly before, as well as in hourly intervals up to the fourth hour after the rejection, 10 μl blood are taken from an ear border vein and the blood glucose is determined by means of the trouble-free and specific hexokinase technique. That dosage is considered as threshhold dosage which significantly lowers the blood glucose concentration in comparison to the control group.

TABLE

| Example No. | Threshold i.p. Dosage for Hypoglycaemic Activity in Testing Guinea Pigs, mg/kg | |
|---|---|---|
| 1 | 15 | |
| 1c | 25 | |
| 1d | 25 | |
| 1e | 5 | |
| 1i | 25 | |
| 1/l | 10 | |
| 1m | 25 | |
| 1/o | 10 | (several animals) |
| 1p | 10 | |
| 1r | 10–25 | |
| 1s | 25 | |
| 2 | 10 | (several animals) |
| 2b | 25 | " |
| 3b | 15–25 | |
| 3d | 20 | |
| 6a | 10 | |
| 6f | 25 | |
| 6h | 10 | |
| 6i | 15–20 | |
| 6j | 30 | |
| 6k | 10 | |
| 6l | 15–20 | |
| Cyclohexylethylhydrazine | 50 | |
| Phenelzine | >50 | |

It will be appreciated that the instant specification and examples are set forth by way of illustration and not limitation, and that various modifications and changes may be made without departing from the spirit and scope of the present invention.

What is claimed is:

1. A 2-hydrazonopropionic acid derivative of the formula

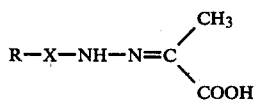

wherein
R is an aliphatic or cycloaliphatic hydrocarbon radical, and
X is a valency bond or a divalent aliphatic hydrocarbon radical containing up to 4 carbon atoms, with the proviso that when X is a valency bond R cannot be a cycloaliphatic hydrocarbon radical, or a physiologically compatible salt, lower alkyl ester or amide thereof.

2. A compound according to claim 1, wherein
R is alkyl or alkenyl of up to 18 carbon atoms, or cycloalkyl or cycloalkenyl of 3 to 8 carbon atoms, or a physiologically compatible salt, lower alkyl ester or amide thereof.

3. A compound according to claim 1, wherein such compound is 2-(2-cyclohexyl-ethylhydrazono)-propionic acid of the formula

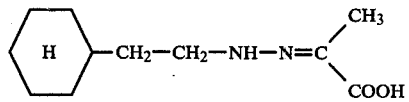

or a physiologically compatible salt, lower alkyl ester or amide thereof.

4. A compound according to claim 1, wherein such compound is 2-(octylhydrazono)-propionic acid of the formula

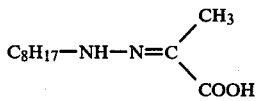

or a physiologically compatible salt, lower alkyl ester or amide thereof.

5. A compound according to claim 1, wherein such compound is 2-(hexylhydrazono)-propionic acid of the formula

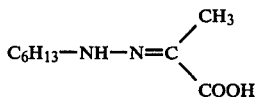

or a physiologically compatible salt, lower alkyl ester or amide thereof.

6. A compound according to claim 1, wherein such compound is 2-(4-hexenylhydrazono)-propionic acid of the formula

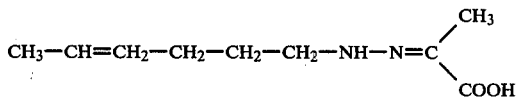

or a physiologically compatible salt, lower alkyl ester or amide thereof.

7. A compound according to claim 1, wherein such compound is 2-(4-methylhexylhydrazono)-propionic acid of the formula

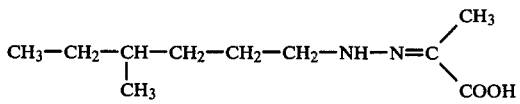

or a physiologically compatible salt, lower alkyl ester or amide thereof.

8. A compound according to claim 1, wherein such compound is 2-(3-cyclopentyl-propylhydrazone)-propionic acid of the formula

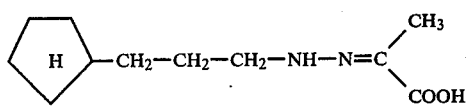

or a physiologically compatible salt, lower alkyl ester or amide thereof.

9. A hypoglycaemic composition of matter comprising a hypoglycaemically active amount of a compound according to claim 1 or a salt, lower alkyl ester or amide thereof in admixture with a diluent.

10. A method of lowering the blood sugar level of a patient comprising administering to such patient a hypoglycaemically active amount of a compound according to claim 1 or a salt, lower alkyl ester or amide thereof.

11. The method according to claim 10, wherein there is administered
2-(2-cyclohexyl-ethylhydrazono)-propionic acid,
2-(octylhydrazono)-propionic acid,
2-(hexylhydrazono)-propionic acid,
2-(4-hexenylhydrazono)-propionic acid,
2-(4-methylhexylhydrazono)-propionic acid, or
2-(3-cyclopentyl-propylhydrazone)-propionic acid,
or
a physiologically compatible salt, lower alkyl ester or amide thereof.

* * * * *